United States Patent [19]

Scholl, Jr.

[11] Patent Number: 5,158,550
[45] Date of Patent: Oct. 27, 1992

[54] DISPOSABLE PROTECTIVE CONTAINER FOR A HYPODERMIC SYRINGE

[76] Inventor: Charles W. Scholl, Jr., 23412 Via Alondra, Trabuco Canyon, Calif. 92678

[21] Appl. No.: 438,264

[22] Filed: Nov. 16, 1989

Related U.S. Application Data

[63] Continuation-in-part of Ser. No. 146,853, Jan. 22, 1988, Pat. No. 4,886,497.

[51] Int. Cl.$^5$ .............................................. A61M 5/00
[52] U.S. Cl. .................................... 604/110; 604/192
[58] Field of Search ............... 604/111, 110, 187, 192; 206/365, 364

[56] References Cited

U.S. PATENT DOCUMENTS 3,008,570  11/1961  Roehr et al. ................. 604/111 X
3,712,302  1/1973  Burke et al. .................... 604/110

Primary Examiner—John D. Yasko
Attorney, Agent, or Firm—W. Edward Johansen

[57] ABSTRACT

A disposable protective container for a hypodermic syringe includes an improved elongated tube having one sealed end and one open end, a concave cap, a welded joint and a lockable fastening mechanism. The concave cap is adapted to fit over the open end of the improved elongated tube. The welded joint frangibly fastens the inner wall of the cap to the outer wall of the improved elongated tube and is adapted to hold the cap in a first axial position relative to the improved elongated tube. The lockable fastening mechanism is adapted to hold the cap in a second axial position after breaking the welded joint in order to protect against inadvertent contact with the needle of the hypodermic syringe before and after it has been used as a disposable protective container for the hypodermic syringe. The improved elongated tube is an integral member which has a first cylindrical portion and a second cylindrical portion. The first cylindrical portion has a flexible section, a closed end and an open end. The second cylindrical portion has a first end and a second open end. The first open end of the second cylindrical portion is coupled by a truncated-cone shaped portion to the open end of the first cylindrical portion. A user may flex the first cylindrical portion in order to break the needle of the hypodermic syringe therein so that there is no longer any reason for an individual to attempt to retrieve the hypodermic syringe.

1 Claim, 3 Drawing Sheets

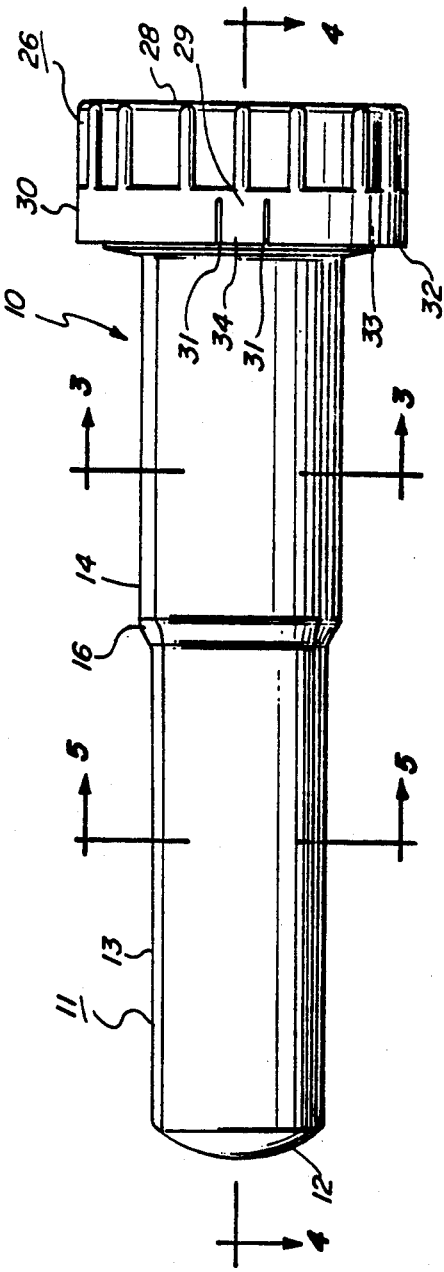
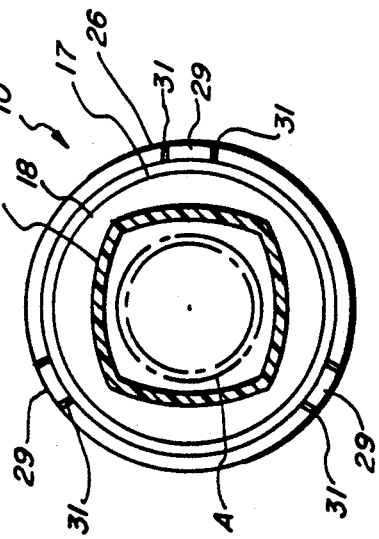
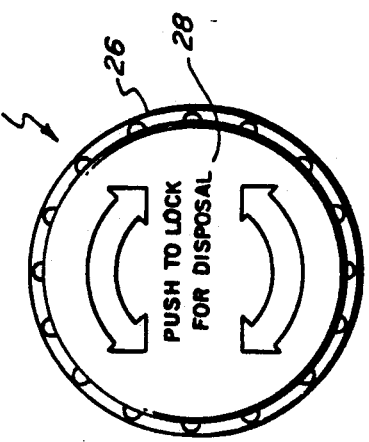

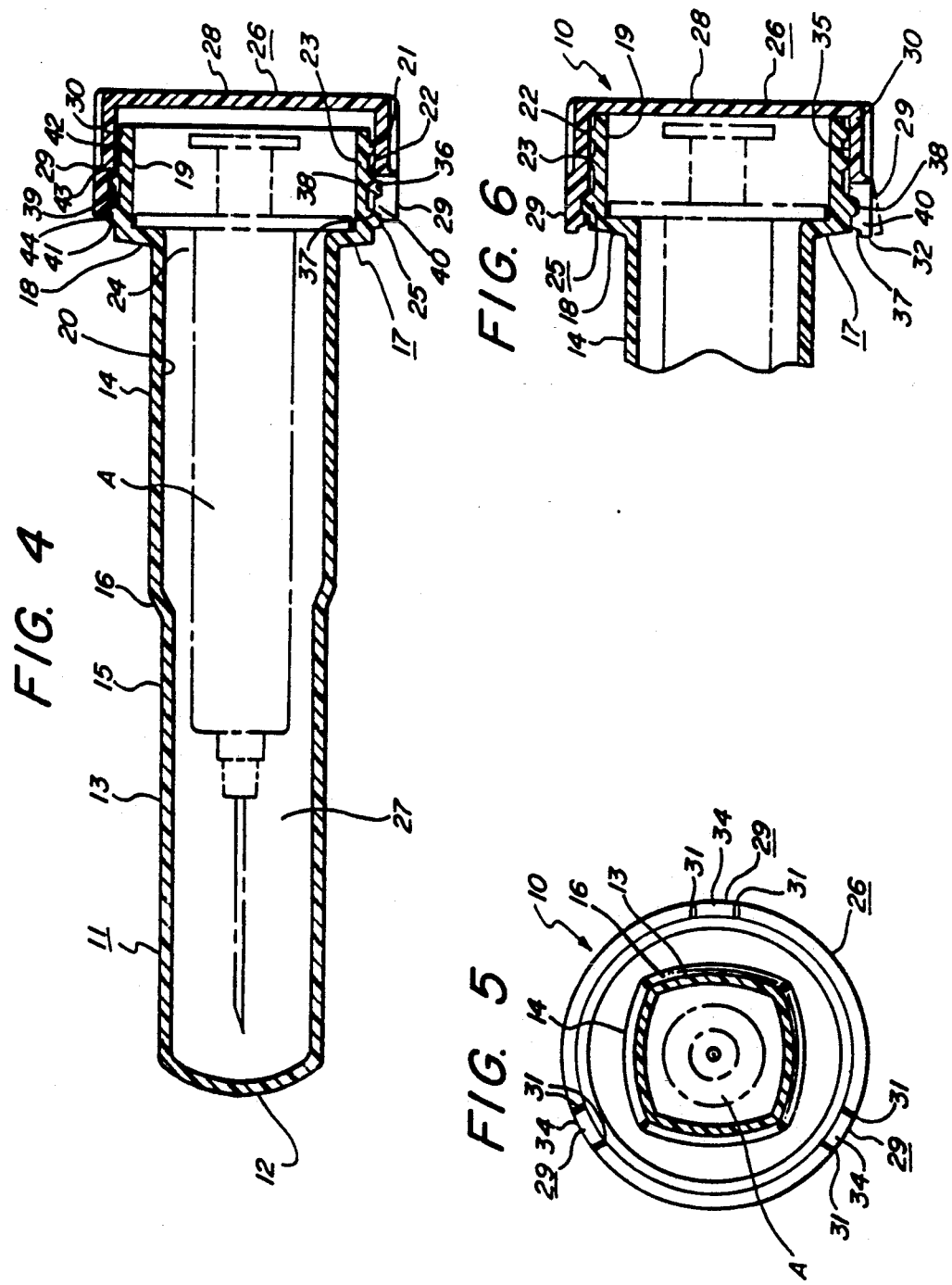

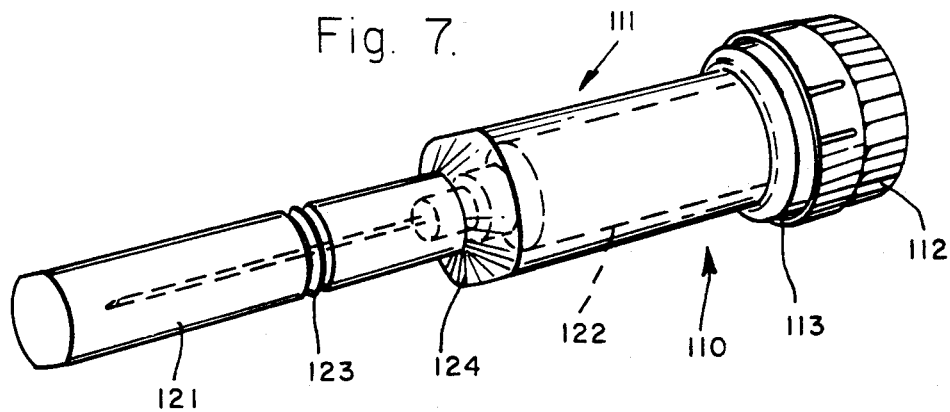
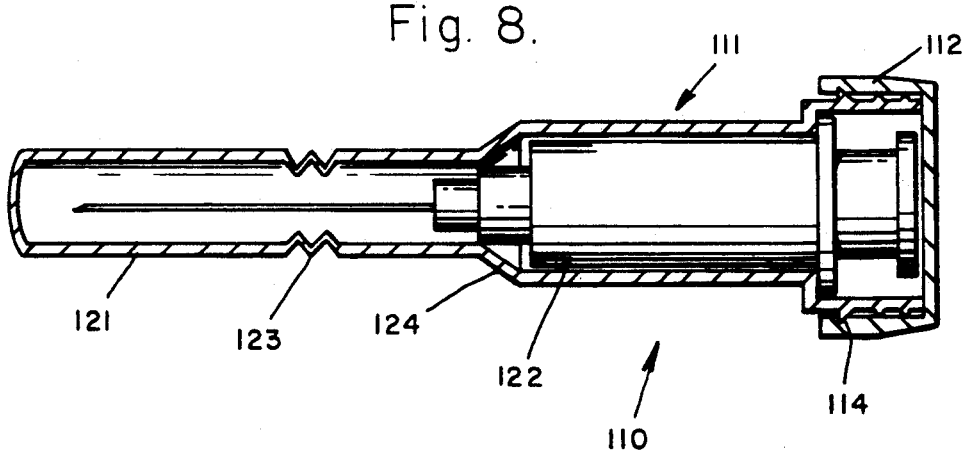
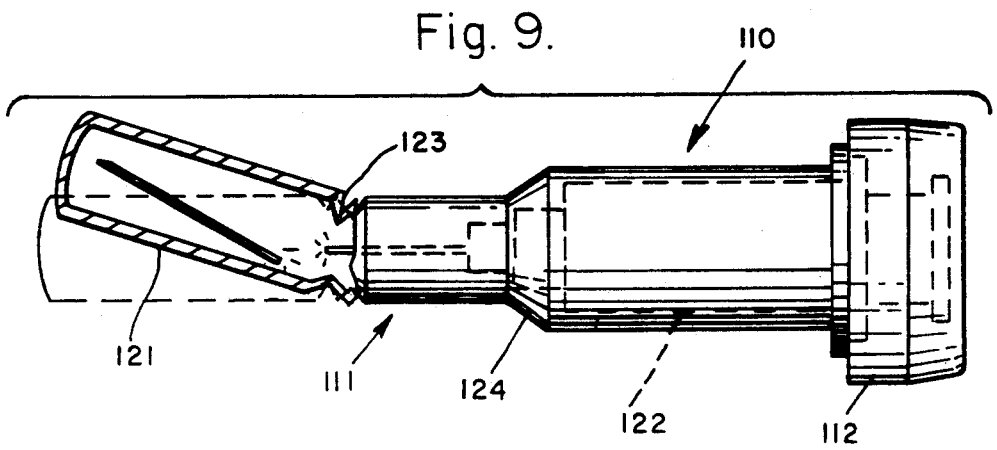

DISPOSABLE PROTECTIVE CONTAINER FOR A HYPODERMIC SYRINGE

This application is a continuation-in-part of the application filed Jan. 22, 1988 under Ser. No. 146,853, now U.S. Pat. No. 4,886,497.

BACKGROUND OF THE INVENTION

1. Field of the Inventions

The present invention relates to a disposable protective container for a hypodermic syringe which protects against inadvertent contact with the needle of the hypodermic syringe before and after it has been used and more particularly to a disposable container for a hypodermic syringe which may be flexed to break the needle of the hypodermic syringe therein so that there is no longer any reason for an individual to attempt to retrieve the hypodermic syringe.

2. Description of the Prior Art

The use of hypodermic syringe has always posed a certain degree of risk to health care professionals, chiefly doctors and nurses. Inadvertent contact with the sharp needle point by some part of the body of a person administering an injection can cause an unwanted injection of a drug contained in the hypodermic syringe. However, since the amount of the fluid which can be inadvertently injected is usually quite small, such accidental injections do not usually pose a serious health hazard.

A much greater hazard to a user of a hypodermic syringe is the potential contact with a needle that has been used to administer an injection or draw blood from a patient afflicted with a contagious disease. Accidental inoculation with a needle which has been used transcutaneously on a patient can result in the health care professional contracting a serious disease such as hepatitis.

Concern about the problem of accidental inoculation by a contaminated needle of a hypodermic syringe has increased along with the population growth and increased level of health care usage of procedures involving hypodermic syringes. This concern has increased dramatically in the recent past with the proliferation of individuals carrying the AIDS virus. Bearing in mind that there is presently no known cure for this debilitating and deadly disease which has a 100 percent mortality rate the high level of concern is well justified.

For the reasons stated above, there is a keen awareness among health care professionals of the necessity of taking substantial precautionary measures to avoid contacting the contaminated needle of a hypodermic syringe. Also there is an awareness of the risk of using a hypodermic syringe which has been previously used or tampered with. These two concerns have prompted the development of a number of prior art devices intended to minimize the possibility of contacting a contaminated needle, or using a previously used or contaminated hypodermic syringe.

U.S. Pat. No. 3,272,322, entitled Syringe Package issued to Robert W. Ogle on Sep. 13, 1966, teaches a tamper indicating syringe package which includes a cylindrical member and a needle sheath for covering a needle of a syringe. The needle sheath is spot-welded to the cylindrical member.

U.S. Pat. No. 4,106,622, entitled Tamper-Resistant Rigid Syringe Package and Method of Making Same, issued to Edward F. Windischman on Aug. 15, 1978, teaches a syringe package which includes a plastic cylindrical container sleeve which is closed at one end and open at the opposite end and which receives a sterile syringe. The sleeve has an enlarged end portion at the open end which is connected by a tapered portion to the main body portions of the sleeve. A rigid plastic end closure is positioned over the enlarged end portion of the sleeve and an end portion of the closure is heat-formed around the tapered portion of the sleeve so that the formed end of the cap has a smaller diameter than the enlarged portion of the sleeve. The heat-formed end portion of the closure may be provided with stress relief in the end portion. U.S. Pat. No. 3,828,775 and U.S. Pat. No. 3,008,570 also teach packaged syringe in which closure members are either fused or otherwise spot-welded to other member of the package and which are broken when the packaged syringe are opened.

U.S. Pat. No. 4,026,287, entitled Syringe with Retractable Cannula, issued to Irene Haller on May 31, 1977, teaches a syringe in which the cannula or needle may be withdrawn inside a protective barrel after use.

U.S. Pat. No. 3,820,652, entitled Packaged Syringe Construction, issued to Thomas Thackston on Jun. 28, 1974, teaches a syringe package which includes a syringe with a needle and a hollow plunger rod and a sheath. The hollow plunger rod and the sheath concentrically cover the needle before the syringe has been used. The sheath covers the needle after the syringe has been used. The sheath is flexible in order to permit flexure to break the needle so that the syringe is rendered useless.

U.S. Pat. No. 4,634,428, entitled Cover for a Disposable Syringe, issued to Cwo-Liang Cuu on Jan. 6, 1987, teaches a disposable syringe with a needle and a cover which covers the needle after use. The cover is flexible in order to permit flexure thereby bending and breaking the needle while still retaining the broken needle therein.

U.S. Pat. No. 4,695,274, entitled Protected Hypodermic Needle, issued to Richard L. Fox on Sep. 22, 1987, teaches a safety needle attachment for a syringe body assembly which makes use of a needle holder With a needle fixed in the holder and the holder so constructed that it can, if necessary, be applied to and removed from the syringe body assembly at will. The needle is initially entirely surrounded by a protecting jacket which is releasably interlocked with the holder. When the needle is to be used, the interlock is released and the jacket in effect telescoped over the holder to project the needle through a membrane over the end of the jacket to a working position. After use the jacket is returned to its protecting position and there interlocked in place. Thereafter for those occasions where the attachment is removable from the body assembly, it can be removed for disposal.

U.S. Pat. No. 4,631,057, entitled Shielded Needle, issued to Charles B. Mitchell on Dec. 23, 1986, teaches an apparatus for injecting a substance into a human or animal which includes a body, a needle coupled to the body and terminating in a point and a needle guard mounted on the body for movement from a retracted position in which the guard does not shield the needle to an extended position in which the guard shields the needle. The needle guard can be releasably retained in the retracted position and locked in the extended position. Locking of the needle guard is accomplished by interlocking members carried by the needle guard and by a collar mounted on the body.

U.S. Pat. No. 4,659,330, entitled Hypodermic Syringe Needle Guard, issued to Robert Nelson and Robert Flome on Apr. 21, 1987, teaches a guard for the needle of a hypodermic syringe which keeps the extremities and particularly the hands well away from the hypodermic syringe to prevent accidental punctures with contaminated needles. The needle guard is in the form of a cylindrical cap which slides over the needle having a manipulating device to remove and replace the guard while keeping the hands well away from the needle. The manipulating device is in the form of a flexible handle having a resilient clamping flanges which clamp the device around the barrel of the syringe. The extension has a webbed hinge allowing it to easily flex outward away from the syringe needle for removal or replacement of the end cap. Alternately the end cap may be hingedly attached to a collar slidable on the syringe barrel by which the cap can be slid downward to remove the cap and retracted to replace the cap. The needle guard may also be in the form of a second cylinder forming a slidably mounted sleeve on the syringe barrel to cover the needle when extended or expose the needle when retracted.

SUMMARY OF THE INVENTION

In view of the foregoing factors and conditions which are characteristic of the prior art it is the primary object of the present invention to provide a disposable protective container for a hypodermic syringe in order to protect against inadvertent contact with its needle before and after it has been used.

It is another object of the present invention to provide a disposable protective container for a hypodermic syringe which a user may flex in order to break the needle of the hypodermic syringe therein so that there is no longer any reason for an individual to attempt to retrieve the hypodermic syringe.

It is still another object of the present invention to provide a disposable protective container for a hypodermic syringe which safely contains a hypodermic syringe before its use and which receives the hypodermic syringe, safely stores it and disposes it after it has been used.

It is yet another object of the present invention to provide a disposable protective container for a hypodermic syringe which has a removable closure which is easy to open and which provides a positive indication of prior tampering.

It is yet still another object of the present invention to provide a disposable protective container for a hypodermic syringe which provides a removable closure which may be replaced on the disposable protective container in a re-closable, locking relationship therewith in order to safely contain a used hypodermic syringe.

In accordance with the present invention an embodiment of a disposable protective container for a hypodermic syringe is described. The disposable protective container includes an improved elongated tube having one sealed end and one open end, a concave cap, a welded joint and a lockable fastening mechanism. The concave cap is adapted to fit over the open end of the improved elongated tube. The welded joint frangibly fastens the inner wall of the cap to the outer wall of the improved elongated tube and is adapted to hold the cap in a first axial position relative to the improved elongated tube. The lockable fastening mechanism is adapted to hold the cap in a second axial position after breaking the welded joint in order to protect against inadvertent contact with the needle of the hypodermic syringe before and after it has been used as a disposable protective container for the hypodermic syringe. The improved elongated tube is an integral member which has a first cylindrical portion and a second cylindrical portion. The first cylindrical portion has a flexible section, a closed end and an open end. The second cylindrical portion has a first end and a second open end. The first open end of the second cylindrical portion is coupled by a truncated-cone shaped portion to the open end of the first cylindrical portion. A user may flex the first cylindrical portion in order to break the needle of the hypodermic syringe therein so that there is no longer any reason for an individual to attempt to retrieve the hypodermic syringe.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 1 is a side elevational view of a first disposable protective container for a hypodermic syringe which has a cap in an unlocked position for use in protecting against inadvertent contact with the needle of the hypodermic syringe before and after it has been used and which has been made in accordance with the principles of the first embodiment of the present invention.

FIG. 2 is an end view of the first disposable protective container of FIG. 1.

FIG. 3 is a first transverse cross-sectional view of the first disposable protective container of FIG. 1 taken along line 3—3 of FIG. 1.

FIG. 4 is a longitudinal cross-sectional view of the first disposable protective container of FIG. 1 taken along line 4—4 of FIG. 1.

FIG. 5 is a second transverse cross-sectional view of the first disposable protective container of FIG. 1 taken along line 5—5 of FIG. 1.

FIG. 6 is a fragmentary longitudinal cross-sectional view of the cap of the first disposable protective container of FIG. 1 with the cap being in a locked position.

FIG. 7 is a perspective drawing of a second disposable protective container for a hypodermic syringe which may be flexed to break the needle of the hypodermic syringe therein so that there is no longer any reason for an individual to attempt to retrieve the hypodermic syringe and which has been made in accordance with the principles of the second embodiment of the present invention.

FIG. 8 is a longitudinal cross-sectional view of the second disposable protective container of FIG. 7.

FIG. 9 is a side elevational view of the second disposable protective container of FIG. 7.

DESCRIPTION OF THE PREFERRED EMBODIMENT

In order to best understand the present invention it is necessary to refer to the following description of its preferred embodiment in conjunction with the accompanying drawing. Referring to FIG. 1 in conjunction with FIG. 2 and FIG. 3 a first disposable protective container 10 for a hypodermic syringe includes an elongated hollow plastic cylinder 11 has a front end wall 12, a front portion and a rear longitudinal portion 14. The elongated hollow plastic cylinder 11 has a generally square transverse cross-sectional shape, the sides of the "square" being, however, bowed outward to present a generally convex perimeter. The front portion 13 of the elongated hollow plastic cylinder 10 extends rearward from the front end wall 12 and has a generally uniform inner diameter which is adapted to longitudinally receive the front barrel portion of a standard hypodermic syringe.

Referring to FIG. 1 in conjunction with FIG. 4 the rear longitudinal portion 14 includes one-half of the length of the elongated hollow plastic cylinder 11 and has a generally uniform inner diameter somewhat larger than the inner diameter of the front portion 13. The front and rear portions 13 and 14 are formed from a continuous longitudinal wall section 15 which has a tapered annular flange section 16 joining the front portion 13 with the rear portion 14.

Referring to FIG. 1 in conjunction with FIG. 5 the longitudinal wall section 15 forming the larger diameter rear portion 14 flares sharply outwards to form a relatively short hollow boss section of a enlarged diameter which is joined to the rear end of the rear portion of the elongated hollow plastic cylinder 11 by a substantially radially disposed annular flange section 18. The hollow boss section 17 has a smooth cylindrical inner wall surface 19 continuous with a inner wall surface 20 of the elongated hollow plastic cylinder 11. A first annular bead 21 and a second annular bead 22 project radially outward from an outer cylindrical wall surface 23 of the boss section 17. The rear first annular bead 21 is spaced axially inwards a slight distance from the open rear end 24 of the boss section 17, while the intermediate second annular bead 22 is spaced axially a slight distance of the rear first annular bead 21. The boss section 17 also includes a front annular bead 25 projecting radially outwards from the outer cylindrical wall surface of the boss section 17. The front annular bead 25 is spaced axially inwards of the intermediate second annular bead 23 just rearward of the annular flange section 18 joining the boss section 17 to the rear portion 14 of the elongated hollow plastic cylinder 11. The front annular bead 25 has a larger outer diameter than the annular beads 21 and 22, and the purpose of each of these annular beads 21 and 22 will be described below. The elongated hollow plastic cylinder 11, including each of its structural element as described above, is preferably fabricated from a sterilizable plastic such as polypropylene by either injection molding or blow molding.

Referring to FIG. 1 in conjunction with FIG. 4 the first disposable protective container 10 also includes a hollow cylindrical cap 26 which is adapted to fit coaxially over the rear boss section 17 of the elongated hollow plastic cylinder 11, closing off the interior space of the elongated hollow plastic cylinder 11 forward of the disc-shaped end wall of the cap 26. The cap 26 is preferably injection molded from a sterilizable resilient plastic material such as polypropylene. The cap 26 includes a plurality, preferably three, of snap locks 29 formed in the cylindrical wall 30 of the cap 26. These snap locks 29 are spaced at equal distance circumferentially around the wall of the cap 26. The snap locks 29 are each formed by a pair of thin, axially disposed slots or kerfs 31 piercing the cylindrical wall 30 of the cap 26. Each slot 31 of a pair is parallel to one another and extends inward a short distance from the annular end wall 32 surrounding the open end of the cap 26. The slots 31 in each pair are spaced relatively close to one another, leaving an axially elongated relatively narrow rectangular tab 34 between the slots 31. The inner cylindrical wall surface 35 of the tabs 34 each contains an axially aligned annular groove 36 a short distance inwards from the annular end wall 32 of the cap 26. The annular end wall 32 of the cap 26 is bevelled to form a gently sloping cam surface 37 joining the inner cylindrical wall surface 35 of the tab 34. A slight distance axially inwards from the intersection of the cam surface 37 with the cylindrical wall surface 35 of the tab 34, a steeply sloping surface 38 extends radially outwards to the bottom wall 39 of the annular groove 36, forming the front wall surface of the groove. The gently sloping cam surface 37, steeply sloping front wall surface 38, and the portion of the inner cylindrical wall surface 35 of the tab 34 form together a radially inwardly projecting locking bead 40 which is a segment of a circle common to each of the plurality of tabs 34.

Referring to FIG. 1 in conjunction with FIG. 2, FIG. 3, FIG. 4, FIG. 5 and FIG. 6 in use the elongated hollow plastic cylinder 11 and the cap 26 are first sterilized and then a sterilized hypodermic syringe is inserted into the opening 24 in the rear boss section 17 of the elongated hollow plastic cylinder 11. The cap 26 is placed coaxially over the rear boss section 17 and pushed down just far enough for the front cam surface of the tab 34 to abut the sloping rear surface 41 of the front annular bead 25 projecting radially outwards from the boss section. The inner cylindrical wall surface 35 of the cap 26 is welded to the outer circumferential surfaces 42 and 43 of the rear and intermediate annular beads 21 and 22 projecting radially outwards from the boss section 17. Preferably the plastic cap 26 is fastened to the boss section 17 of the cylinder by ultrasonic or radio frequency welding. To gain access to the hypodermic syringe the cap 26 must be twisted relative to the cylinder to break the welds joining the cap 26 to the boss section 17 of the elongated hollow plastic cylinder 11, The breaking produces a distinctive snap which can be both heard and felt by the user opening the first disposable protective container 10 providing a positive indication that the hypodermic syringe contained in the package has not been previously used or tampered with. Conversely the absence of the tactile and audible signal produced by the welds breaking warns the user of tampering or prior use. After the hypodermic syringe has been removed from the first disposable protective container 10 in the manner described above, the first disposable protective container 10 provides a novel and very effective means for safely storing and transporting to a disposal site a used hypodermic syringe. A used hypodermic syringe is inserted into the elongated hollow plastic cylinder 11 and the cap 26 is pushed down over the rear boss section 17 of the first disposable protective cylinder 10 exactly has been described above. This time, however, the cap 26 is pushed further forward, to the extent that the bevelled front cam surface on the front annular end wall 32 of each tab 34 slides upward on the abutting rear sloping surface of the front annular bead 25 of the boss section 17. Radially outward movement of the tabs 34 relative to the cylindrical wall 30 of the cap 26 is permitted by the flexibility of the plastic material from which the cap 26 and is facilitated by the slots 31 on either side of each tab 34. As the cap 26 is pushed further downward over the boss section 17, the radially inwardly projecting locking bead 25 of each tab 34 eventually slides over the radially outwardly projecting front annular bead 25 of the boss section 17. Pushing the cap 26 slightly further down on the boss section 17 causes the locking bead to seat in the annular groove of each tab 34, the elasticity of the tab 34 restoring it to its original position from its radially outwardly distorted position. In this seated position, the steeply sloping front wall surface 38 of the annular groove in each tab 34 abuts the front wall surface 44 of the front annular bead 25 of the boss section 17. Contact between these two abutting surfaces prevents rearward axial movement of the cap 26 relative to the elongated hollow plastic cylinder 11, after the cap 26 has been pushed all the way down on the boss section 17 to snapping engage the bead 25 of the boss section in grooves 36 of the tabs 34 of the cap 26. With the cap 26 and the elongated hollow plastic cylinder 11 thus lockingly engaged, the cap 26 is securely locked to the elongated hollow plastic cylinder 11. Since more force than is exerted by a normal human being would be required to pull off the cap 26 from the elongated hollow plastic cylinder 11 once they are lockingly engaged as described above the first disposable protective container 10 and the enclosed used hypodermic syringe may be safely disposed of without the danger of contacting the potentially biologically hazardous needle of the used hypodermic syringe.

Referring to FIG. 7 in conjunction with FIG. 8 a second disposable protective container 110 for a hypodermic syringe includes an improved elongated tube 111 having one sealed end and one open end, a concave cap 112, a welded joint 113 and a lockable fastening mechanism 114. The concave cap 112 is adapted to fit over the open end of the improved elongated tube 111. The welded joint 113 frangibly fastens the inner wall of the cap 112 to the outer wall of the improved elongated tube 111 and is adapted to hold the cap 112 in a first axial position relative to the improved elongated tube 111. The lockable fastening mechanism 114 is adapted to hold the cap 112 in a second axial position after breaking the welded joint 113 in order to protect against inadvertent contact with the needle of the hypodermic syringe before and after it has been used as the second disposable protective container 110 for the hypodermic syringe. The improved elongated tube 111 is an integral member which has a first cylindrical portion 121 and a second cylindrical portion 122. The first cylindrical portion 121 has a flexible section 123, a closed end and an open end. The second cylindrical portion 122 has a first end and a second open end. The first open end of the second cylindrical portion 122 is coupled by a truncated-cone shaped portion 124 to the open end of the first cylindrical portion 121. A user may flex the first cylindrical portion 121 in order to break the needle of the hypodermic syringe therein so that there is no longer any reason for an individual to attempt to retrieve the hypodermic syringe.

From the foregoing it can be seen that a disposable protective container for a hypodermic syringe which not protects against inadvertent contact with the needle of the hypodermic syringe before and after it has been used, but also which may be flexed to break the needle of the hypodermic syringe therein so that there is no longer any reason for an individual to attempt to retrieve the hypodermic syringe has been described.

It should be noted that the sketches are not drawn to scale and that distance of and between the figures are not to be considered significant.

What is claimed is:

1. An improved disposable protective container for a hypodermic syringe comprising:
   a. an integral member having a first cylindrical portion which has a flexible section, a closed end and an open end and a second cylindrical portion which has a first an open end and a second open end and said second open end of which is coupled by a truncated-cone shaped portion to said open end of said first cylindrical portion;
   b. a concave cap which is adapted to fit over the open end of said integral member;
   c. a welded joint which frangibly fastens the inner wall of said concave cap to the outer wall of said improved integral member and is adapted to hold said concave cap in a first axial position relative to said integral member; and
   d. lockable fastening means for holding said concave cap in a second axial position after breaking said welded joint in order to protect against inadvertent contact with the needle of the hypodermic syringe before and after it has been used as a container for the hypodermic syringe whereby a user may flex said first cylindrical portion in order to break the needle of the hypodermic syringe therein so that there is no longer any reason for an individual to attempt to retrieve the hypodermic syringe.

* * * * *